(12) United States Patent
Chamberlain et al.

(10) Patent No.: US 10,816,544 B2
(45) Date of Patent: Oct. 27, 2020

(54) METHODS FOR MEASURING SMALL MOLECULE AFFINITY TO CEREBLON

(71) Applicant: CELGENE CORPORATION, Summit, NJ (US)

(72) Inventors: Philip Paul Chamberlain, San Diego, CA (US); Mary Matyskiela, San Diego, CA (US); Godrej Khambatta, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 15/887,941

(22) Filed: Feb. 2, 2018

(65) Prior Publication Data

US 2018/0224435 A1    Aug. 9, 2018

Related U.S. Application Data

(60) Provisional application No. 62/454,654, filed on Feb. 3, 2017.

(51) Int. Cl.
*G01N 33/542* (2006.01)
*C07K 14/47* (2006.01)

(52) U.S. Cl.
CPC ........... *G01N 33/542* (2013.01); *C07K 14/47* (2013.01); *G01N 2333/4703* (2013.01); *G01N 2500/04* (2013.01)

(58) Field of Classification Search
CPC ............. G01N 33/542; G01N 2500/04; G01N 2333/4703; G01N 21/6428; G01N 2021/6432; G01N 2021/1746; G01N 2021/1789; G01N 2500/00; C07K 19/00; C09K 11/0822; C09K 11/7728; C09K 11/7783
See application file for complete search history.

(56) References Cited

U.S. PATENT DOCUMENTS

| | | |
|---|---|---|
| 9,365,640 B2 | 6/2016 | Lopez-Girona et al. |
| 9,587,281 B2 | 3/2017 | Thakurta et al. |
| 9,611,465 B2 | 4/2017 | Handa et al. |
| 10,047,151 B2 | 8/2018 | Lopez-Girona et al. |
| 10,092,555 B2 | 10/2018 | Chamberlain et al. |
| 10,272,117 B2 | 4/2019 | Handa et al. |
| 2012/0134969 A1 | 5/2012 | Handa et al. |
| 2017/0007645 A1 | 1/2017 | Handa et al. |
| 2017/0362660 A1 | 12/2017 | Thakurta et al. |
| 2018/0224435 A1 | 8/2018 | Chamberlain et al. |

(Continued)

FOREIGN PATENT DOCUMENTS

WO    WO 2014028445    2/2014

OTHER PUBLICATIONS

Boidhenko et al. A fret-based assay for the identification and characterization of cereblon ligands. J. Med. Chem. 2016, vol. 59, pp. 770-774. (Year: 2016).*

(Continued)

*Primary Examiner* — Shafiqul Haq
(74) *Attorney, Agent, or Firm* — Jones Day

(57) ABSTRACT

A complex comprises a CRBN having a europium-anti-his antibody on the N-terminus of the CRBN, and a Cy5-conjugated small molecule, wherein the Cy5-conjugated small molecule binds the CRBN, and uses thereof for identifying therapeutic compounds.

7 Claims, 6 Drawing Sheets

(56) References Cited

U.S. PATENT DOCUMENTS

2019/0030019 A1 1/2019 Chamberlain et al.
2019/0037818 A1 2/2019 Chopra et al.

OTHER PUBLICATIONS

Fischer et al. Structure of the DDBI-CRBN E3 ubiquitin ligase in complex with thalidomide. Nature 2014, vol. 512, pp. 49-53 (Year: 2014).*
Lebakken et al. Development and applications of a broad-coverage TR-FRET=based kinase binding assay platform. J. Biomolecular Screening 2009, vol. 14, No. 8, pp. 924-935 (Year: 2009).*
Comley, John. TR_FRET based assays—getting better with age., Drug Discovery World, Spring 2016, pp. 22-37. (Year: 2006).*
Boichenko et al., "A FRET-Based Assay for the Idnetificaiton and Characterization of Cerblon Ligands", Journal of Medicinal Chemistry, 59:770-774, (2016).
Fischer et al., "Structyure of the DDB1-CRBN E3 ubiquitin ligase in complex with thalidomide", Nature, 512:49-53 (2014).
International Search Report and Written Opinion of corresponding Interantional Patent Application No. PCT/US2018/016609 dated Apr. 28, 2018 (7 pages).
Li et al., "A Novel High-Throughput Screening Assay for Discovery of Molecules That Increase Cellular Tetrahydrobiopterin", Journal of Biomolecular Screening, 16:836-844 (2011).
GE Healthcare, 2006, Amersham Eu (TMT) Isothiocyanate Product Booklet, PA99141PL Rev D 2006 (16 pages).
BioTek Application Guide, 2012, Synergy™ Microplate Readers and HTRF® Detection, revised Sep. 12, 2012 (12 pages).
Hall et al., 2016, "Fluorescence polarization assays in high-throughput screening and drug discovery: a review," Methods Appl. Fluoresc., 4(2):022001 (41 pages).

* cited by examiner

Compound B

Lenalidomide

METHODS FOR MEASURING SMALL MOLECULE AFFINITY TO CEREBLON

CROSS REFERENCE

This application claims the benefit of priority of U.S. Provisional Patent Application No. 62/454,654, filed Feb. 3, 2017, the content of which is incorporated herein by reference in its entirety.

1. FIELD

The present disclosure relates generally to a complex comprising cereblon and two light-sensitive molecules, methods for measuring the affinity between cereblon and a compound, and use thereof for identifying compounds with potential therapeutic effects.

2. BACKGROUND

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (ClC-2) in the retina with AMPK1 and DDB1. See Jo, S. et al., *J. Neurochem*, 2005, 94:1212-1224; Hohberger B. et al., *FEBS Lett*, 2009, 583:633-637; Angers S. et al., *Nature*, 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

CRBN has recently been identified as a key molecular target that binds to a few therapeutic compounds, e.g., thalidomide, pomalidomide, and lenalidomide. These drugs target CRBN, and alter the substrate specificity of the ubiquitin ligase, driving the clinical activity in certain cancer cells. Bound substrates are ubiquitinated by the CRBN-CRL4 complex, leading to their degradation by the 26S proteasome. Understanding the interactions of CRBN with these compounds will allow the definition of the molecular mechanisms of efficacy and/or toxicity and may lead to drugs with improved efficacy and toxicity profiles.

3. SUMMARY

In one aspect, provided herein is a complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

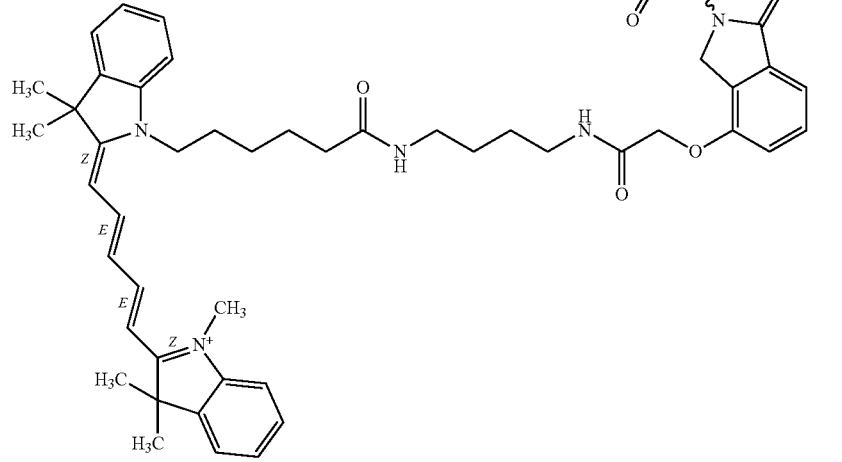

In another aspect, provided herein is a method of determining if a compound binds to cereblon (CRBN), comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

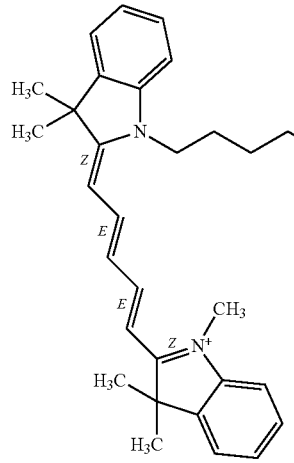
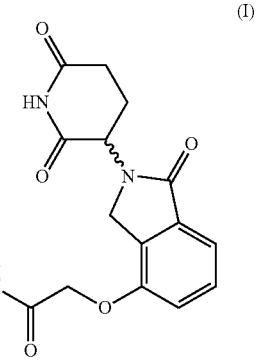

(I)

In some embodiments, the method further comprises measuring fluorescence resonance energy transfer (FRET) after contacting the compound with the complex.

In some embodiments, the method further comprises measuring FRET prior to contacting the compound with the complex.

In some embodiments, the method further comprises determining that the compound binds to the CRBN if FRET is reduced after contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the method further comprises determining that the compound binds to the CRBN if the second FRET efficiency is less than the first FRET efficiency.

In yet another aspect, provided herein is a method of measuring the affinity of a compound to cereblon (CRBN), comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below (I)

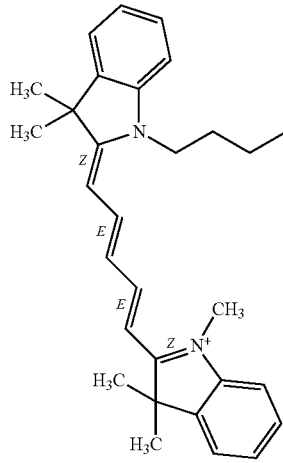
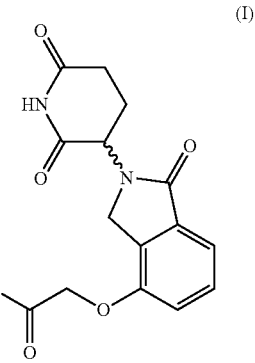

In some embodiments, the method further comprises measuring fluorescence resonance energy transfer (FRET) after contacting the compound with the complex.

In some embodiments, the method further comprises measuring FRET prior to contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the affinity of the compound to CRBN is determined by measuring the difference between the first FRET efficiency and the second FRET efficiency.

In yet another aspect, provided herein is a method of identify a compound for treating a disease, comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below In some embodiments, the method further comprises determining that the compound can potentially be used for treating the disease if FRET is reduced after contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the method further comprises determining that the compound can potentially be used for treating the disease if the second FRET efficiency is less than the first FRET efficiency.

In some embodiments, the disease is a CRBN mediated disease.

In yet another aspect, provided herein is a composition comprising the complex provided herein.

4. BRIEF DESCRIPTION OF THE DRAWINGS

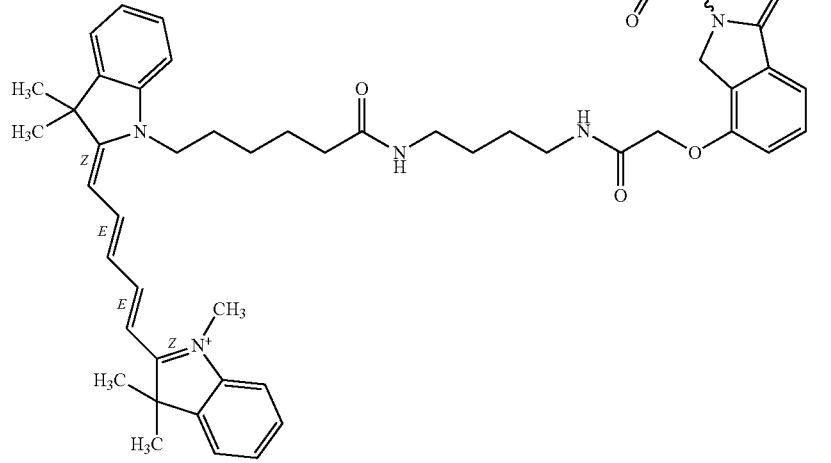

(I)

luminescent cell-based assay. $EC_{50}$s determined were 67 nM for lenalidomide (circles), 24 nM for pomalidomide (diamonds), and 1 nM for Compound B (squares). Part b) shows quantitation of Aiolos degradation with chemiluminescent cell-based assay. $EC_{50}$s determined were 87 nM for lenalidomide (circles), 22 nM for pomalidomide (diamonds), and 0.5 nM for Compound B (squares). Part c) shows immunoblot analysis of whole-cell extracts of DF15 and OPM2 cells incubated for 5 hours with DMSO, lenalidomide, pomalidomide or Compound B at the indicated concentrations.

Figure 5A:
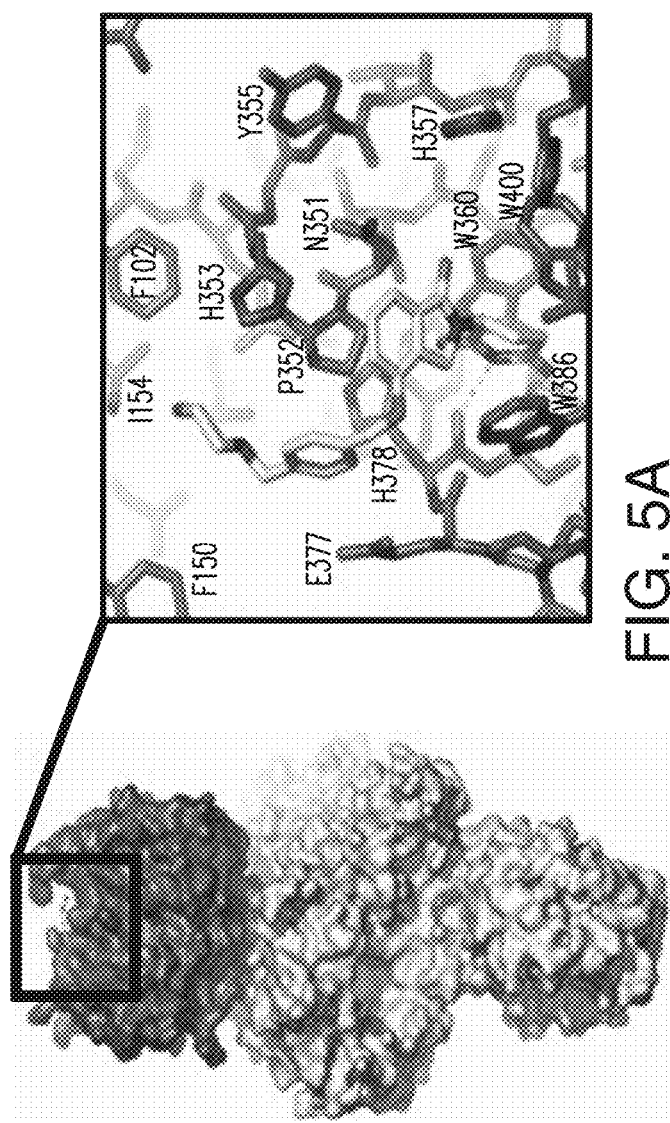
Figure 5B:
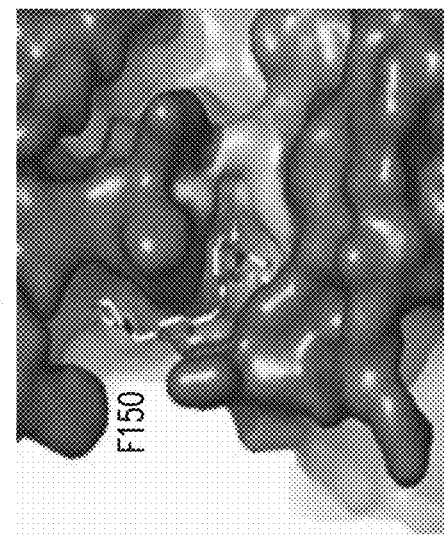
Figure 5B:
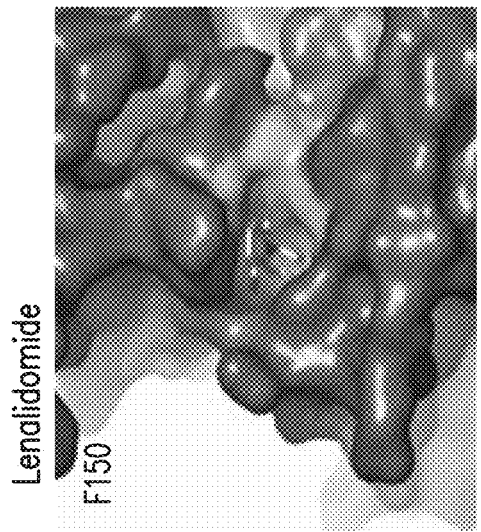

FIG. 5 depicts crystal structure of cereblon in complex with DDB1 and a compound. Part a) shows the crystal structure of cereblon in complex with DDB1 and Compound B. Inset shows detail of bound Compound B, with the glutarimide ring docked in the tri-trp pocket and the phenyl ring extending from the isoindolinone positioned in a groove formed by E377, H378, P352 and H353 of cereblon. Part b) shows comparison of the binding surface interactions of lenalidomide (left panel) and Compound B (right panel) with cereblon. The amino acid sidechain F150 is labeled.

5. DETAILED DESCRIPTION

A few compounds including immunomodulatory drugs for treating various cancers have been shown to target cereblon (CRBN), a substrate receptor for the CRL4 (CUL4-RBX1-DDB1) ubiquitin ligase complex, and alter the substrate specificity of the ubiquitin ligase, driving the clinical activity in cancer cells. Since several studies have now shown that the mechanism of action for anti-cancer drugs such as thalidomide involves binding to the protein CRBN, it would be beneficial to understand the binding between these drugs and CRBN, which will ultimately help to develop new drugs with advanced therapeutic effects.

Thus, there is a need in the art to develop methods for testing the affinity between various compounds and CRBN and to identify new CRBN binding therapeutic compounds.

Provided herein among others is a quick and easily scalable assay to measure the affinity between a compound and CRBN and to identify new small molecules that bind to CRBN and quantify the relative affinities of those compounds.

Figure 1:
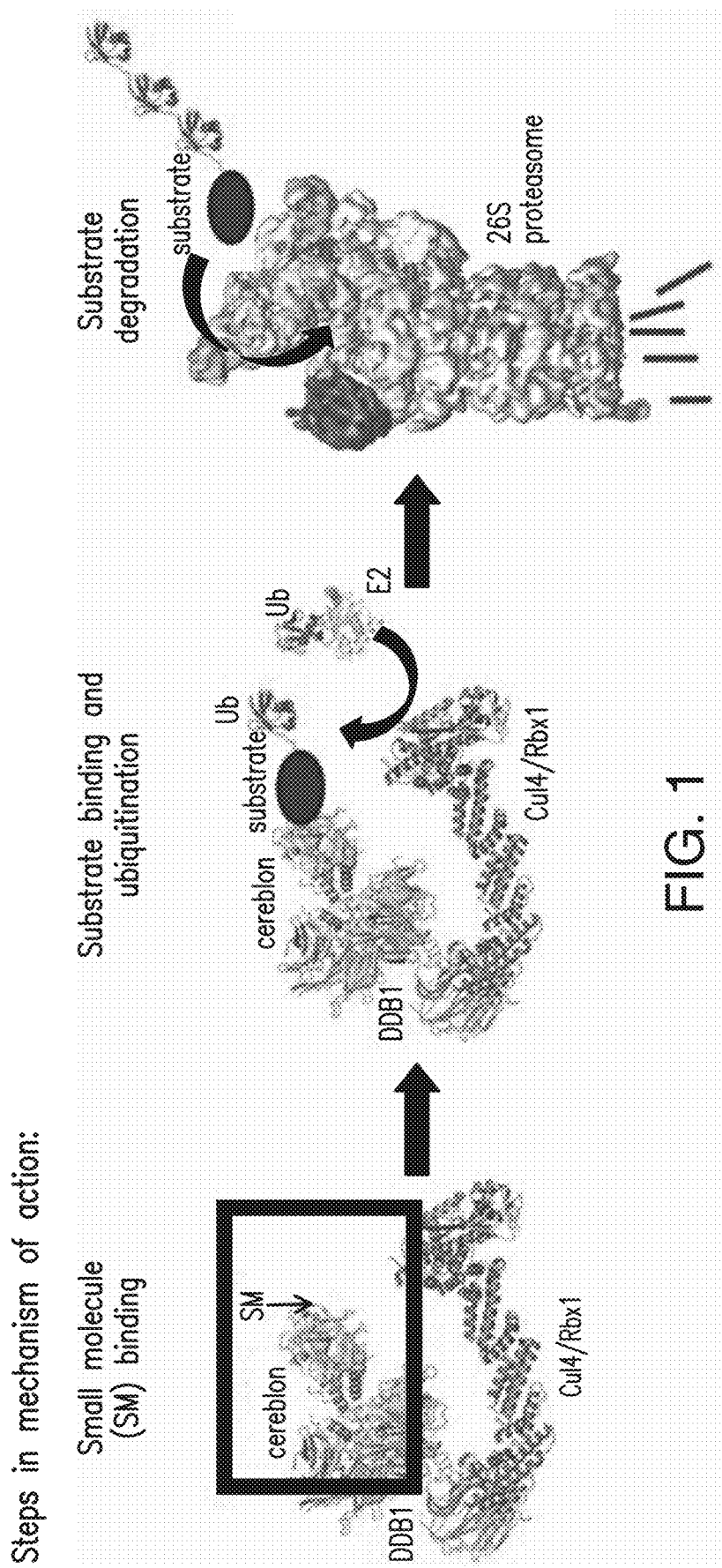
FIG. 1 depicts the steps of small molecule binding to cereblon.

Small molecule potency can be driven by many different steps in mechanism of action, including cereblon affinity, substrate affinity, and the efficiency of ubiquitination and degradation (see FIG. 1). By isolating the step of small molecule binding to cereblon, we can determine the cereblon binding contribution of each molecule to potency, and find starting points for chemistry without needing cellular activity.

Structural studies have shown that certain clinical compounds bind to cereblon through their glutarimide ring, which docks into a hydrophobic tri-tryptophan pocket formed by Trp380, Trp386, and Trp400 on CRBN.

Figure 2:
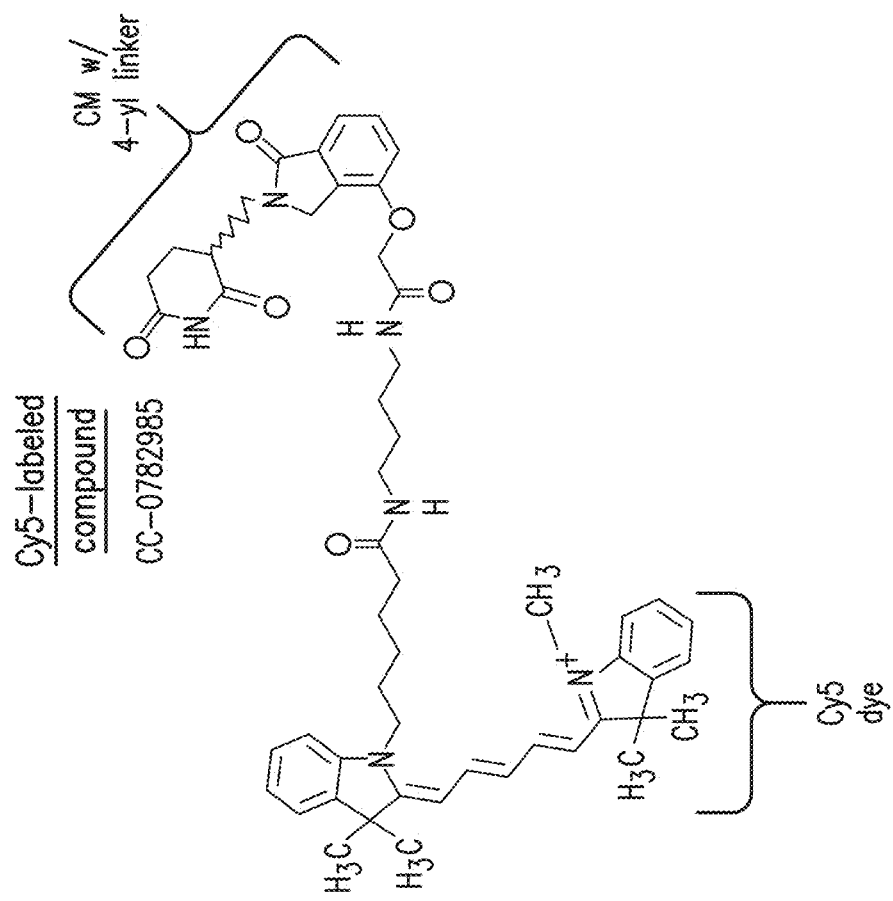
FIG. 2 depicts the HTRF-based assay for determining the binding of a small molecule to cereblon.
Figure 2:
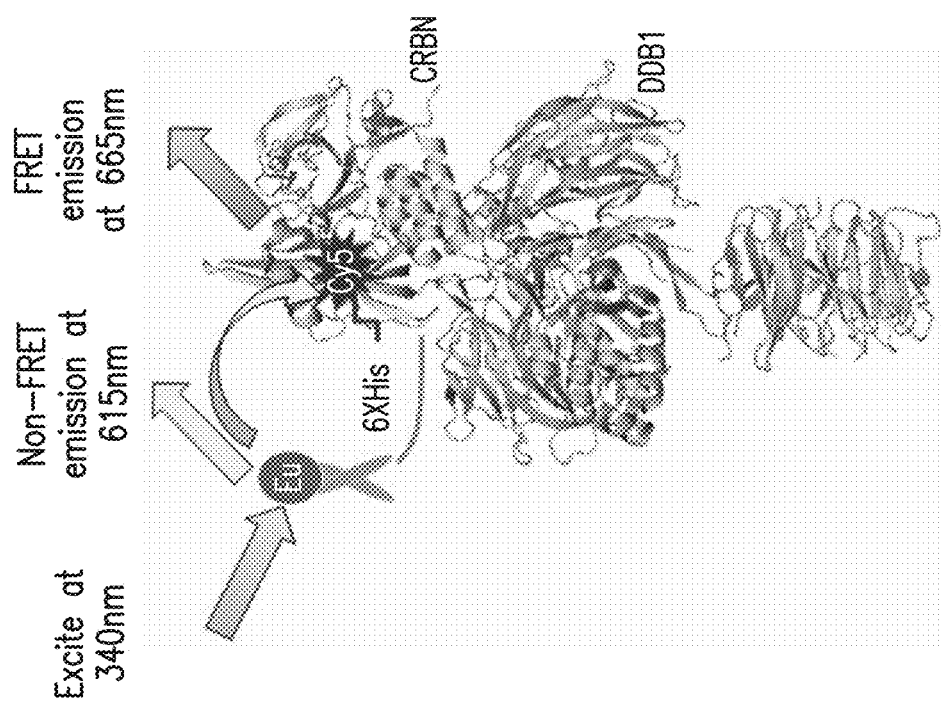

As described in the Examples below (see Section 6), the new HTRF-based assay of the present disclosure provides a sensitive and high throughput screening format for the determination of both high and low affinity between CRBN and a compound. The new HTRF-based assay of the present disclosure utilizes a complex comprising CRBN, a donor chromophore or fluorophore and an acceptor chromophore or fluorophore. More specifically, the method provided herein uses a complex comprising a CRBN with a europium-anti-his antibody on its N-terminus and a Cy5-conjugated small molecule that binds in the cereblon tri-tryptophan pocket. A CRBN-binding compound can interfere with the interaction and/or configuration between the europium-anti-his antibody at the N-terminus of CRBN and the Cy5-conjugated small molecule, resulting in a reduced FRET signal (see FIG. 2). Thus, by analyzing FRET, the affinity of the compound and CRBN can be determined. The assay provided herein can measure IC50s for both high affinity molecules and low affinity fragments like glutarimide. It can also be used to compare small molecule affinity and cellular potency for existing and novel small molecules.

5.1 Definitions

All patents, applications, published applications and other publications are incorporated by reference in their entirety. Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors. Other exemplary cancers are provided elsewhere herein.

The terms "cereblon" or "CRBN" and similar terms refers to the polypeptides ("polypeptides," "peptides" and "proteins" are used interchangeably herein) comprising the amino acid sequence any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and inter-species homologs, which, in certain embodiments, retain CRBN activity and/or are sufficient to generate an anti-CRBN immune response.

As used herein, the term "cereblon-associated protein" or "CRBN-associated protein" refers to a protein that interacts with or binds to CRBN directly or indirectly. In certain embodiments, a "cereblon-associated protein" or "CRBN-associated protein" is a substrate of CRBN, for example, a protein substrate of the E3 ubiquitin ligase complex involving CRBN, or the downstream substrates thereof. In certain embodiments, a "cereblon-associated protein" or "CRBN-associated protein" is a binding protein of CRBN.

The term "CRBN modifying agent" or "CMA" refers to a molecule that directly or indirectly modulating the CRBN E3 ubiquitin-ligase complex. In some embodiments, the CMA can bind directly to CRBN and induce conformational change in the CRBN protein. In other embodiments, the CMA can bind directly to other subunits in the CRBN E3 ubiquitin-ligase complex.

As used herein, the term "immunomodulatory compound" or "immunomodulatory drug" refers generally to a molecule or agent capable of altering the immune response in some way.

As used herein, the term "composition" is intended to encompass a product containing the specified ingredients (e.g., the complex provided herein) and, optionally, in the specified amounts, as well as any product which results, directly or indirectly, from combination of the specified ingredients in, optionally, the specified amounts.

The term "effective amount" or "therapeutically effective amount" as used herein refers to the amount of a therapy which is sufficient to reduce and/or ameliorate the severity and/or duration of a given disease, disorder or condition and/or a symptom related thereto. This term also encompasses an amount necessary for the reduction or amelioration of the advancement or progression of a given disease, disorder or condition, reduction or amelioration of the recurrence, development or onset of a given disease, disorder or condition, and/or to improve or enhance the prophylactic or therapeutic effect(s) of another therapy. In some embodiments, "effective amount" or "therapeutically effective amount" as used herein also refers to the amount of therapy provided herein to achieve a specified result.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

The term "refractory or resistant" refers to a circumstance where patients, even after intensive treatment, have residual cancer cells (e.g., leukemia or lymphoma cells) in their lymphatic system, blood and/or blood forming tissues (e.g., marrow).

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, and greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a disease, disorder or condition. In another embodiment, the subject is a mammal (e.g., a human) at risk of developing a disease, disorder or condition.

As used herein, the term "therapy" refers to any protocol, method and/or agent that can be used in the prevention, management, treatment and/or amelioration of a given disease, disorder or condition. In certain embodiments, the terms "therapies" and "therapy" refer to a drug therapy, biological therapy, supportive therapy, and/or other therapies useful in the prevention, management, treatment and/or amelioration of a given disease, disorder or condition known to one of skill in the art such as medical personnel.

As used herein, and unless otherwise specified, the terms "treat," "treating" and "treatment" refer to an action that occurs while a patient is suffering from the specified disease, disorder or condition. As used herein, the terms "treat," "treatment" and "treating" refer to the reduction or amelioration of the progression, severity, and/or duration of a disease, disorder or condition resulting from the administration of one or more therapies.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

5.2 Complexes Comprising CRBN and Light-Sensitive Molecules

Provided herein, for example, are compositions, methods and kits for screening or otherwise identifying a compound that binds to an E3 ubiquitin ligase.

In one aspect, provide herein is a complex comprising CRBN, wherein the complex further comprises a donor chromophore or flurophore and an acceptor chromophore or flurophore. In some embodiments, the donor chromophore or flurophore or the acceptor chromophore or flurophore binds to the N-terminus of CRBN. In some embodiments, the donor chromophore or flurophore or the acceptor chromophore or flurophore binds to the compound-binding pocket of CRBN. In some more specific embodiments, one of the donor chromophore or flurophore and the acceptor chromophore or flurophore binds to the N-terminus of CRBN, and the other one binds to the hydrophobic tri-tryptophan pocket formed by Trp380, Trp386, and Trp400 on the CRBN.

In some embodiments, provided herein is a CRBN complexed with a dye-labeled small molecule compound. In some embodiments, provided herein is a complex comprising (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1, wherein DDB1 binds to CRBN.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

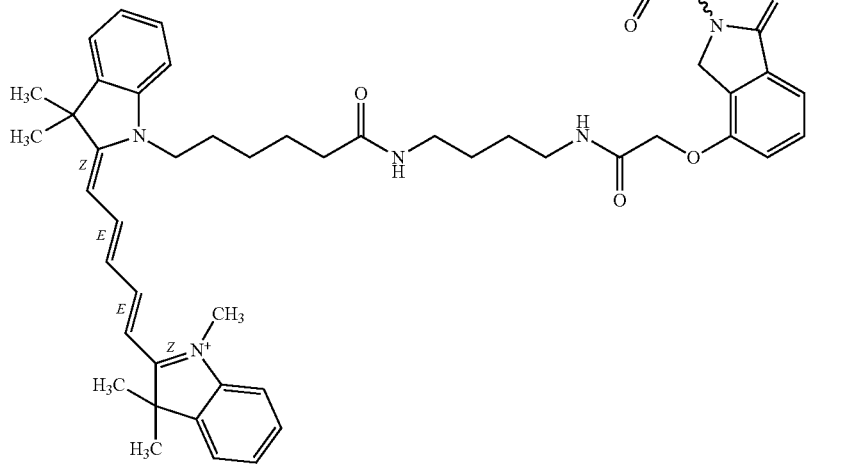

(I)

In some specific embodiments, the complex is prepared by mixing 6×His-CRBN-DDB1 complex with europium-anti-his antibody and the Cy5-conjugated small molecule of Formula (I). In a more specific embodiment, the complex is prepared by mixing 60 nM 6×His-CRBN-DDB1, 3 nM europium-anti-his antibody, and 30 nM Cy5-conjugated small molecule of Formula (I).

In another aspect, provided herein is a crystalline CRBN complexed with a dye-labeled small molecule compound.

In yet another aspect, provided herein is a composition comprising the various complexes provided herein.

5.3 Methods of Measuring the Affinity Between CRBN and a Compound

In one aspect, provided herein is a method of determining if a compound binds to cereblon (CRBN), comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

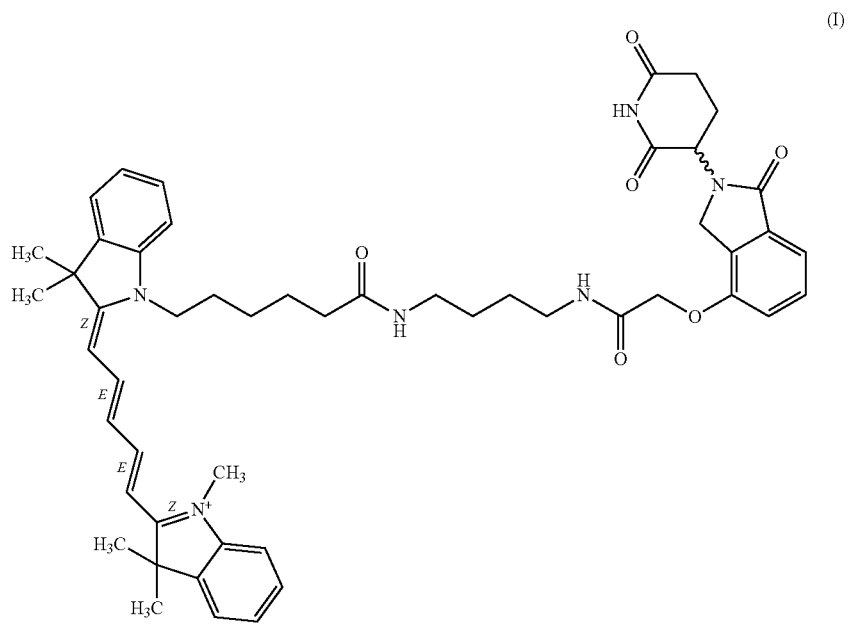 [SMILES: C[N+]1=C(/C=C/C=C/C=C2\N(CCCCCC(=O)NCCCCNC(=O)COc3cccc4c3CN(C3CCC(=O)NC3=O)C4=O)c3ccccc3C2(C)C)C(C)(C)c2ccccc21]

(I)

Fluorescence resonance energy transfer (FRET) is a distance-dependent interaction between the electronic excited states of two molecules in which excitation is transferred from a donor fluorophore to an acceptor without emission of a photon. The process of energy transfer results in a reduction (quenching) of fluorescence intensity and excited state lifetime of the donor fluorophore and, where the acceptor is a fluorophore, can produce an increase in the emission intensity of the acceptor. The efficiency of this energy transfer is inversely proportional to the sixth power of the distance between donor and acceptor, making FRET extremely sensitive to small changes in distance. FRET efficiency can be used as an indicator of the distance between donor and acceptor fluorophores (and the corresponding molecules or atoms to which they are attached), with decreased FRET efficiency correlating with increased distance (i.e., an inverse correlation).

Contacting a CRBN-binding compound to the complex provided herein changes the distance and/or configuration between the europium-anti-his antibody on the N-terminus of the CRBN and the Cy5-conjugated small molecule, and thus alters the FRET and/or FRET efficiency. Therefore, by measuring FRET or FRET efficiency, the affinity of a compound to CRBN can be determined.

FRET can be detected in at least one of two ways: fluorescence or quenching. In fluorescence, a detector is set to the emission spectra of the acceptor fluorophore and binding is indicated by energy transfer from the donor to the acceptor and fluorescence from the acceptor. In quenching, the detector is set to the emission spectra of the donor fluorophore and binding is indicated by energy transfer from the donor to the acceptor and quenching of emission from the donor.

Those skilled in the art would understand the methods of measuring FRET and FRET efficiency. These methods are also included in the present disclosure.

Thus, in some embodiments, the method further comprises measuring fluorescence resonance energy transfer (FRET) after contacting the compound with the complex.

In some embodiments, the method further comprises measuring FRET prior to contacting the compound with the complex.

In some embodiments, the method further comprises determining that the compound binds to the CRBN if FRET is reduced after contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the method further comprises determining that the compound binds to the CRBN if the second FRET efficiency is less than the first FRET efficiency.

In another aspect, provided herein is a method of measuring the affinity of a compound to cereblon (CRBN), comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below (I)

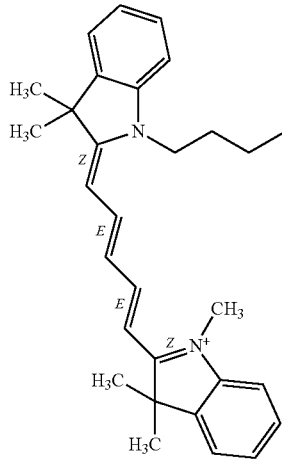
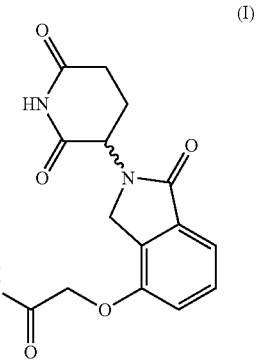

In some embodiments, the method further comprises measuring fluorescence resonance energy transfer (FRET) after contacting the compound with the complex.

In some embodiments, the method further comprises measuring FRET prior to contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the affinity of the compound to CRBN is determined by measuring the difference between the first FRET efficiency and the second FRET efficiency.

In yet another aspect, provided herein is a method for comparing affinities of two CRBN-binding compounds, comprising determining a first affinity of a first compound to CRBN, and determining a second affinity of a second compound to CRBN.

In some embodiments of the various methods provided herein, the compound to be tested can be a CRBN modifying agent (or CMA). In some embodiment of the various methods provided herein, the compound is an immunomodulatory compound. In some embodiments of the various methods provided herein, the compound is not an immunomodulatory compound.

In some more specific embodiments, the binding affinity of thalidomide to CRBN is measured and/or compared with the affinity of another compound to CRBN. In other more specific embodiments, the binding affinity of pomalidomide to CRBN is measured and/or compared with the affinity of another compound to CRBN. In other more specific embodiments, the binding affinity of lenalidomide to CRBN is measured and/or compared with the affinity of another compound to CRBN. In other more specific embodiments, the binding affinity of Compound A to CRBN is measured and/or compared with the affinity of another compound to CRBN. In other more specific embodiments, the binding affinity of Compound B to CRBN is measured and/or compared with the affinity of another compound to CRBN. In yet other more specific embodiments, the binding affinity of Compound D to CRBN is measured and/or compared with the affinity of another compound to CRBN. In more specific embodiments, the binding affinity of Compound E to CRBN is measured and/or compared with the affinity of another compound to CRBN.

5.4 Methods of Identifying Compounds of Therapeutic Effects

As shown in Sections 6.6 and 6.7 below, higher biochemical binding affinity of a compound to CRBN correlates well with greater potency in cellular activities as demonstrated in cellular degradation assays. Thus, the methods provided here for measuring the affinity of a compound to CRBN can also be used for identifying compounds having a biological activity or therapeutic effects.

In another aspect, provided herein is a method of identify a compound for treating a disease, comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

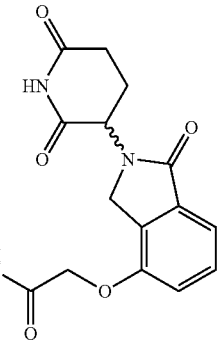
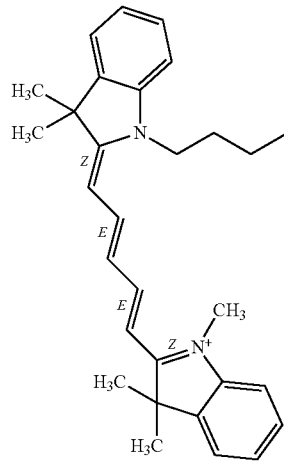

In some embodiments, the method further comprises measuring fluorescence resonance energy transfer (FRET) after contacting the compound with the complex.

In some embodiments, the method further comprises measuring FRET prior to contacting the compound with the complex.

In some embodiments, the method further comprises determining that the compound can potentially be used for treating the disease if FRET is reduced after contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the method further comprises determining that the compound can potentially be used for treating the disease if the second FRET efficiency is less than the first FRET efficiency.

In some embodiments, the disease is a CRBN mediated disease.

In another aspect, provided herein is a method of identifying a compound that has a specific downstream biological activity comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below (I)

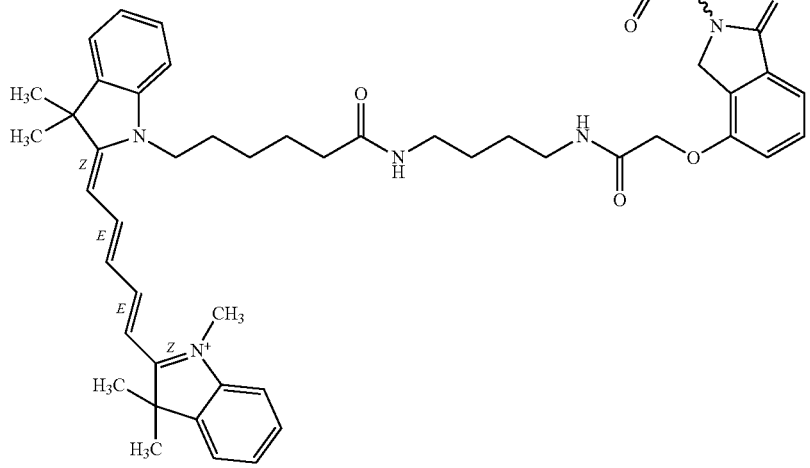

In some embodiments, the method further comprises measuring fluorescence resonance energy transfer (FRET) after contacting the compound with the complex.

In some embodiments, the method further comprises measuring FRET prior to contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments, the biological activity is a tumoricidal effect. In other embodiments, the biological activity is an apoptosis effect. In some embodiments, the biological activity is anti-proliferation. In yet other embodiments, the biological activity is PBMC viability. In some embodiments, the biological activity is toxicity. In certain embodiments, the biological activity is substrate degradation. In one embodiment, the biological activity is Aiolos degradation. In another embodiment, the biological activity is Ikaros degradation. In other embodiments, the biological activity is an immune-mediated effect. In another embodiment, the biological activity is IL-2 induction. In some embodiments, the biological activity is IL-2 repression. In yet other embodiments, the biological activity is a HbF effect. In some embodiments, the effect is an effect on a CRBN-associated protein. Any combination of one, two, three or more of the aforementioned biological activities is also contemplated.

In certain embodiments, a biological activity is observed in one cell type, but not another cell type. In some embodiments, a biological activity is observed in one tissue type, but not another tissue type.

In certain embodiments, a biological activity is observed in one tumor (or cancer) type, but not another tumor (or cancer) type.

In some embodiments, a biological activity is observed in a solid tumor (or cancer), but not in a non-solid tumor (or cancer) (e.g., a hematological tumor).

In some embodiments, a biological activity is observed in a non-solid tumor (or cancer) (e.g., a hematological tumor), but not in a solid tumor (or cancer).

In certain embodiments, the solid tumor or cancer is a breast, kidney, ovary, colon, bladder, brain, liver of prostate tumor or cancer. In some embodiments, the non-solid tumor is a blood (hematological) cancer.

In some embodiments, exemplary tumors or cancers include without limitation acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof.

In certain embodiments, the biological activity being modulated by the CMA has a direct effect on therapeutic utility of the CMA in a subject.

In another aspect, provided herein is a method of identifying a test compound that has a specific therapeutic efficacy or specific therapeutic utility comprising contacting the compound with a complex, wherein the complex comprises (i) a CRBN having a europium-anti-his antibody on the N-terminus of the CRBN, and (ii) a Cy5-conjugated small molecule, wherein the Cy5-conjugated small molecule binds the CRBN.

In some embodiments, the complex further comprises a DDB1.

In some embodiments, the Cy5-conjugated small molecule binds in a hydrophobic tri-tryptophan pocket formed by Trp380, Trp386, and Trp400 on the CRBN.

In a specific embodiment, the Cy5-conjugated small molecule has a structure of Formula (I) shown below

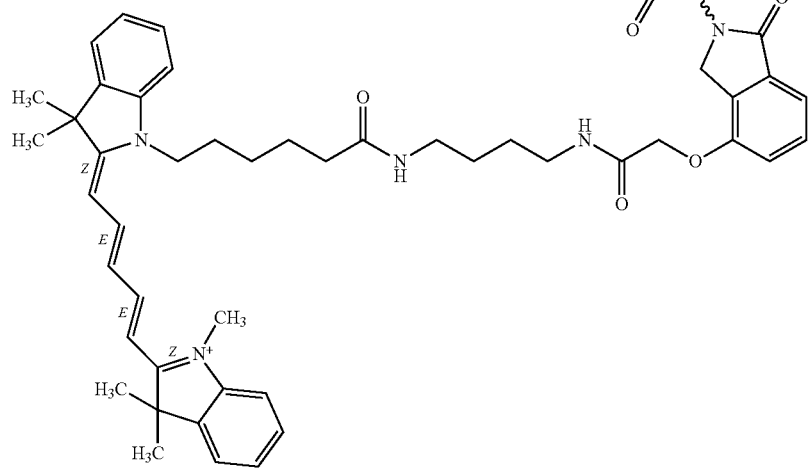

In some embodiments, the method further comprises measuring fluorescence resonance energy transfer (FRET) after contacting the compound with the complex.

In some embodiments, the method further comprises measuring FRET prior to contacting the compound with the complex.

In some embodiments, FRET is observed by exciting at 340 nm and monitoring emission at 615 nm (non-FRET emission) and 665 nm (FRET emission).

In some embodiments, a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

In some embodiments of the various methods provided herein, the therapeutic utility is the management or treatment of a CRBN-associated disease, disorder or a symptom thereof. In other embodiments, the therapeutic utility is the management or treatment of a cancer or tumor, or a symptom thereof. In some embodiments, the tumor or cancer is a liver cancer, kidney cancer, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof. In some embodiments, the cancer or tumor is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma.

In some embodiments of the various methods provided herein, the identified compound is a CRBN modifying agent (or CMA). In some embodiment of the various methods provided herein, the identified compound is an immunomodulatory compound. In some embodiments of the various methods provided herein, the identified compound is not an immunomodulatory compound.

In some more specific embodiments, the binding affinity of thalidomide to CRBN is measured and/or compared with the affinity of another compound to CRBN to determine the therapeutic utility of another compound. In other more specific embodiments, the binding affinity of pomalidomide to CRBN is measured and/or compared with the affinity of another compound to CRBN to determine the therapeutic utility of another compound. In other more specific embodiments, the binding affinity of lenalidomide to CRBN is measured and/or compared with the affinity of another compound to CRBN to determine the therapeutic utility of another compound. In other more specific embodiments, the binding affinity of Compound A to CRBN is measured and/or compared with the affinity of another compound to CRBN to determine the therapeutic utility of another compound. In other more specific embodiments, the binding affinity of Compound B to CRBN is measured and/or compared with the affinity of another compound to CRBN to determine the therapeutic utility of another compound. In yet other more specific embodiments, the binding affinity of Compound D to CRBN is measured and/or compared with the affinity of another compound to CRBN to determine the therapeutic utility of another compound. In more specific embodiments, the binding affinity of Compound E to CRBN is measured and/or compared with the affinity of another compound to CRBN to determine the therapeutic utility of another compound.

5.5 Types of Cells

In certain embodiments, the biological activity is based on specific cell type categories. Such cells can include any type of cells, e.g., stem cells, blood cells (e.g., peripheral blood mononuclear cells), lymphocytes, B cells, T cells, monocytes, granulocytes, immune cells, or tumor or cancer cells.

For example, B cells (B lymphocytes) include plasma B cells, memory B cells, B1 cells, B2 cells, marginal-zone B cells, and follicular B cells. B cells can express immunoglobulins (antibodies, B cell receptor). In one embodiment, the cells are Karpas 422, TMD8, WSU-DLCL2, OCI-LY10, Karpas 1106P, HT, SUDHL-10, Riva, OCI-LY19, SUDHL-4, SUDHL-6, OCI-LY3, and Farage.

Specific cell populations can be obtained or assessed using a combination of commercially available antibodies (e.g., Quest Diagnostic (San Juan Capistrano, Calif.); Dako (Denmark)).

In certain embodiments, the cell line is lenalidomide-resistant WSU-DLCL2 or TMD8 cell line. In certain embodiments, the cell line is a DLBCL cell line. In some embodiments, the cell line is a ABC-DLBCL (activated B cell-like DLBCL) cell line, for example, TMD8, OCI-LY10, Riva, or OCI-LY3 cell line. In other embodiments, the cell line is a GCB-DLBCL (germinal center B cell-like DLBCL) cell line, for example, Karpas 422, WSU-DLCL2, Karpas 1106P, HT, SUDHL-10, OCI-LY19, SUDHL-4, or SUDHL-6 cell line.

In some embodiments, the number and type of cells can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used or detected in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

In one embodiment, the RNA (e.g., mRNA) or protein is purified and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

5.6 Methods of Assaying a Specific Biological Activity

In certain embodiments of the methods provided herein, the method further comprises assaying a specific biological activity of the compound identified by the binding assay provided herein, for example, to verify the potential therapeutic effects of the compound.

In certain embodiments, the biological activity is substrate degradation. In certain embodiments, the substrate is a CRBN-associated protein. In one embodiment, the CRBN-associated protein is Ikaros. In another embodiment, the CRBN-associated protein is Aiolos. In some embodiments, the CRBN-associated protein is detected and/or quantified.

In some embodiments, the protein level of a CRBN-associated protein, e.g., a substrate of CRBN, is detected or measured. Several protein detection and quantitation methods can be used to measure the level of CRBN-associated proteins. Any suitable protein quantitation method can be used. In some embodiments, antibody-based methods are used. Exemplary methods that can be used include but are not limited to immunoblotting (western blot), enzyme-linked immunosorbent assay (ELISA), immunohistochemistry, flow cytometry, cytometric bead array, mass spectroscopy, and the like. Several types of ELISA are commonly used, including direct ELISA, indirect ELISA, and sandwich ELISA.

In some embodiments, the methods comprises: (a) contacting the sample with a first antibody that immunospecifically binds to the CRBN-associated protein; (b) contacting the sample bound to the first antibody with a second antibody with a detectable label, wherein the second antibody immunospecifically binds to the CRBN-associated protein, and wherein the second antibody immunospecifically binds to a different epitope on CRBN-associated protein than the first antibody; (c) detecting the presence of second antibody bound to the sample; and (d) determining the protein level of the CRBN-associated protein based on the amount of detectable label in the second antibody.

In other embodiments, the mRNA level of a CRBN-associated protein, e.g., a downstream target regulated by a substrate of CRBN, is detected or measured. Several methods of detecting or quantitating mRNA levels are known in the art. Exemplary methods include but are not limited to northern blots, ribonuclease protection assays, PCR-based methods, and the like. The mRNA sequence, e.g., the mRNA of CRBN-associated proteins, or a fragment thereof, can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for a compound activity in a biological sample can be prepared. An assay typically contains a solid support and at least one nucleic acid contacting the support, where the nucleic acid corresponds to at least a portion of an mRNA that has altered expression during a compound treatment in a patient, such as the mRNA of CRBN-associated proteins. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in Genetic Engineering: Principles and Methods (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of CRBN-associated proteins. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (qRT-PCR) can be used for both the detection and quantification of RNA targets (Bustin, et al., 2005, *Clin. Sci.,* 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TaqMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

5.7 Compounds

In some embodiments, the methods provided herein are for testing the affinity between a compound and CRBN. In some embodiments of the various methods provided herein, the compounds can be any CRBN modifying agents (or CMAs).

The CMAs provided herein include, but are not limited to, the immunomodulatory compounds, a group of compounds that can be useful to treat several types of human diseases, including certain cancers. In certain embodiments of the various compositions and methods provided herein, a CMA is an immunomodulatory compound provided herein. In other embodiments, a CMA is not an immunomodulatory compound provided herein.

As used herein and unless otherwise indicated, the term "immunomodulatory compound" or "immunomodulatory agent" includes molecules or agents capable of altering the immune response in some way. For example, it can encompass certain small organic molecules that inhibit LPS induced monocyte TNF-α, IL-1β, IL-12, IL-6, MIP-1α, MCP-1, GM-CSF, G-CSF, and COX-2 production. In some embodiments, the immunomodulatory compounds provided herein can reduce myeloid cell TNF-α production. In some embodiments, the immunomodulatory compounds disclosed herein may enhance the degradation of TNF-α mRNA. In other embodiments, the immunomodulatory compounds disclosed herein are potent co-stimulators of T cells and increase cell proliferation dramatically in a dose dependent manner. In yet other embodiments, the immunomodulatory compounds disclosed herein may have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. In yet other embodiments, the immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Exemplary CMAs provided herein include but are not limited to thalidomide, lenalidomide, pomalidomide, Compound A, Compound B, Compound C, Compound D, and Compound E.

In a specific embodiment, the compound is thalidomide.

In another specific embodiment, the compound is lenalidomide.

In yet another specific embodiment, the compound is pomalidomide.

In yet another specific embodiment, the compound is 3-(5-amino-2-methyl-4-oxo-4H-quinazolin-3-yl)-piperidine-2,6-dione ("Compound A"), which has the following structure:

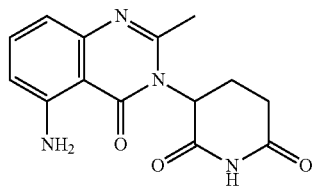

A or an enantiomer or a mixture of enantiomers thereof; or a pharmaceutically acceptable salt, solvate, hydrate, co-crystal, clathrate, or polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional at. App. No. 61/451,995, filed Mar. 11, 2011, which is incorporated herein by reference in its entirety.

In yet another specific embodiment, the compound is 3-(4-((4-(morpholinomethyl)benzyl)oxy)-1-oxoisoindolin-2-yl)piperidine-2,6-dione ("Compound B"), which has the following structure:

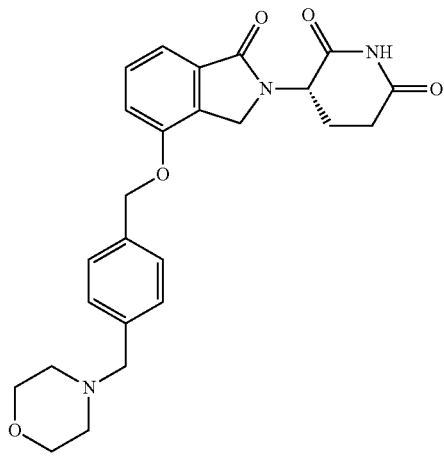

B or an enantiomer or a mixture of enantiomers thereof; or a pharmaceutically acceptable salt, solvate, hydrate, co-crystal, clathrate, or polymorph thereof.

Compound B and methods of preparing the same are described in U.S. Pat. No. 8,518,972, which is incorporated herein by reference in its entirety. Exemplary method of making Compound B is also illustrated in Example 6.1 below.

In yet another specific embodiment, the compound is 1-(3-chloro-4-methylphenyl)-3-((2-(2,6-dioxopiperidin-3-yl)-1-oxoisoindolin-5-yl)methyl)urea ("Compound C"), which has the following structure:

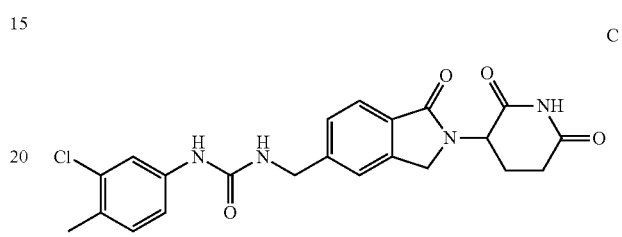

C or an enantiomer or a mixture of enantiomers thereof or a pharmaceutically acceptable salt, solvate, hydrate, co-crystal, clathrate, or polymorph thereof.

In yet another specific embodiment, the compound is 2-(4-chlorophenyl)-N-((2-(2,6-dioxopiperidin-3-yl)-1-oxoisoindolin-5-yl)methyl)-2,2-difluoroacetamide ("Compound D"), which has the following structure:

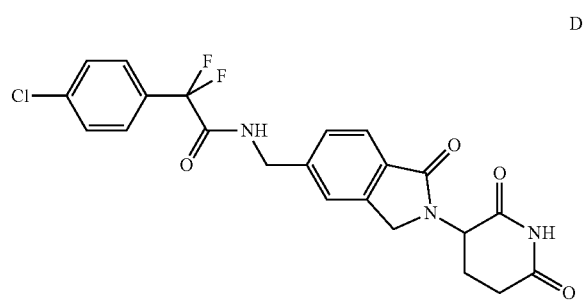 [SMILES: O=C1CCC(N2Cc3cc(CNC(=O)C(F)(F)c4ccc(Cl)cc4)ccc3C2=O)C(=O)N1]

D or an enantiomer or a mixture of enantiomers thereof or a pharmaceutically acceptable salt, solvate, hydrate, co-crystal, clathrate, or polymorph thereof.

In yet another specific embodiment, the compound is 2-(4-fluorphenyl)-N-((2-(2,6-dioxopiperidin-3-yl)-1-oxoisoindolin-5-yl)methyl)-2,2-difluoroacetamide ("Compound E"), which has the following structure:

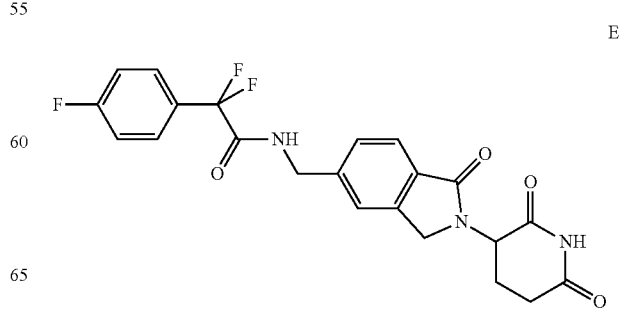

E or a pharmaceutically acceptable salt, solvate, stereoisomer, isotopologue, prodrug, hydrate, co-crystal, clathrate, or a polymorph thereof.

Compounds D and E and methods of preparing the same are described in U.S. Pat. No. 9,499,514, which is incorporated herein by reference in its entirety.

Various compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.8 Treatment of a CRBN-Mediated Disease

Also provided herein is a method of treating and preventing a CRBN-mediated disease, which comprises administering to a patient a compound identified using the various methods provided herein. In certain embodiments, the CRBN-mediated disease or disorder is a cancer. In certain embodiments, provided herein is a compound identified by the various methods provided herein for use in a method of treating and preventing a CRBN-mediated disease, the method comprises administering to a patient the compound, or an enantiomer or a mixture of enantiomers thereof, or a pharmaceutically acceptable salt, solvate, hydrate, co-crystal, clathrate, or polymorph thereof.

In another embodiment, provided herein is method of managing a CRBN-mediated disease, which comprises administering to a patient a compound identified using the various methods provided herein. In certain embodiments, the CRBN-mediated disease or disorder is a cancer. In certain embodiments, provided herein is a compound identified by the various methods provided herein for use in a method of managing a CRBN-mediated disease, the method comprises administering to a patient the compound, or an enantiomer or a mixture of enantiomers thereof, or a pharmaceutically acceptable salt, solvate, hydrate, co-crystal, clathrate, or polymorph thereof.

Also provided herein are methods of treating patients who have been previously treated for a CRBN-mediated disease or disorder (e.g., a cancer) but are non-responsive to standard therapies, as well as those who have not previously been treated. Also provided herein are methods of treating patients regardless of patient's age, although some diseases or disorders are more common in certain age groups. Also provided herein are methods of treating patients who have undergone surgery in an attempt to treat the disease or condition at issue, as well as those who have not. In some embodiments provided herein a compounds provided herein for use in methods of treating patients as mentioned above.

Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, sclero-derma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 0.1, about 0.2, about 0.3. about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a compound provided herein, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.01, 0.05, 0.1, 0.2, 0.3, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.01, 0.05, 0.1, 0.2, 0.3, 0.4, 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., a compound provided herein, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

Depending on the disease to be treated and the subject's condition, a compound provided herein, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, a compound provided herein, or an enantiomer or a mixture of enantiomers thereof; or a pharmaceutically acceptable salt, solvate, hydrate, co-crystal, clathrate, or polymorph thereof, is administered orally. In another embodiment, a compound provided herein, or an enantiomer or a mixture of enantiomers thereof; or a pharmaceutically acceptable salt, solvate, hydrate, co-crystal, clathrate, or polymorph thereof, is administered parenterally.

In yet another embodiment, a compound provided herein, or an enantiomer or a mixture of enantiomers thereof; or a pharmaceutically acceptable salt, solvate, hydrate, co-crystal, clathrate, or polymorph thereof, is administered intravenously.

A compound provided herein, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

A compound provided herein, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 10 days to 52 weeks. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a compound provided herein, or an enantiomer or a mixture of enantiomers thereof; or a pharmaceutically acceptable salt, solvate, hydrate, co-crystal, clathrate, or polymorph thereof, is administered once a day. In another embodiment, a compound provided herein, or an enantiomer or a mixture of enantiomers thereof; or a pharmaceutically acceptable salt, solvate, hydrate, co-crystal, clathrate, or polymorph thereof, is administered twice a day. In yet another embodiment, a compound provided herein, or an enantiomer or a mixture of enantiomers thereof; or a pharmaceutically acceptable salt, solvate, hydrate, co-crystal, clathrate, or polymorph thereof, is administered three times a day. In still another embodiment, a compound provided herein, or an enantiomer or a mixture of enantiomers thereof; or a pharmaceutically acceptable salt, solvate, hydrate, co-crystal, clathrate, or polymorph thereof, is administered four times a day.

In certain embodiments, a compound provided herein, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, a compound provided herein, or a pharmaceutically acceptable salt or solvate thereof, is administered once per day for one week, two weeks, three weeks, or four weeks. In one embodiment, a compound provided herein, or an enantiomer or a mixture of enantiomers thereof; or a pharmaceutically acceptable salt, solvate, hydrate, co-crystal, clathrate, or polymorph thereof, is administered once per day for one week. In another embodiment, a compound provided herein, or an enantiomer or a mixture of enantiomers thereof; or a pharmaceutically acceptable salt, solvate, hydrate, co-crystal, clathrate, or polymorph thereof, is administered once per day for two weeks. In yet another embodiment, a compound provided herein, or an enantiomer or a mixture of enantiomers thereof; or a pharmaceutically acceptable salt, solvate, hydrate, co-crystal, clathrate, or polymorph thereof, is administered once per day for three weeks. In still another embodiment, a compound provided herein, or an enantiomer or a mixture of enantiomers thereof; or a pharmaceutically acceptable salt, solvate, hydrate, co-crystal, clathrate, or polymorph thereof, is administered once per day for four weeks.

Further provided herein are methods for achieving one or more clinical endpoints associated with various hematological cancers such as AML, and/or MDS comprising administering a therapeutically effective amount of the compound identified using the various methods provided herein to a patient in need thereof.

Further provided herein are methods for increasing the overall survival (OS), complete remission rate (CRR), objective response rate (ORR), time to progression, relapse free survival (RFS), progression-free survival (PFS) event-free survival, duration of remission, duration of response, and/or time to remission/response of a patient having a hematological cancer comprising administering an effective amount of the compound identified using the various methods provided herein. In certain embodiment, the ORR includes all responses of complete remission (CR) (i.e., morphologic leukemia-free state, morphologic CR, cytogenetic CR, molecular CR, and morphologic CR with incomplete blood recovery), and partial remission.

As used herein, Overall survival (OS) means the time from randomization in a clinical trial until death from any cause. Progression-free survival (PFS) means the time from randomization in a clinical trial until progression or death. Event-free survival (EFS) means the time from study entry until any treatment failure, including disease progression, treatment discontinuation for any reason, or death. Overall response rate (ORR) means the sum of the percentage of patients who achieve complete and partial responses. Duration of response (DoR) is the time from achieving a response until relapse or disease progression.

As used herein, "hematological cancer" includes myeloma, lymphoma and leukemia. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

A compound identified using the various methods provided herein, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., a compound provided herein, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of a compound provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of a compound provided herein is independent of the route of administration of a second therapy. In one embodiment, a compound provided herein is administered orally. In another embodiment, a compound provided herein is administered intravenously.

Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of a compound provided herein provided herein and any optional additional active agents concurrently administered to the patient.

The following examples are offered by way of illustration, and not by way of limitation.

6. EXAMPLES

6.1 Preparation of 3-[4-(4-morpholin-4-ylmethyl-benzyloxy)-oxo-1,3-dihydro-isoindol-2-yl]-piperidine-2,6-dione (Compound B)

Compound B Synthesis Scheme

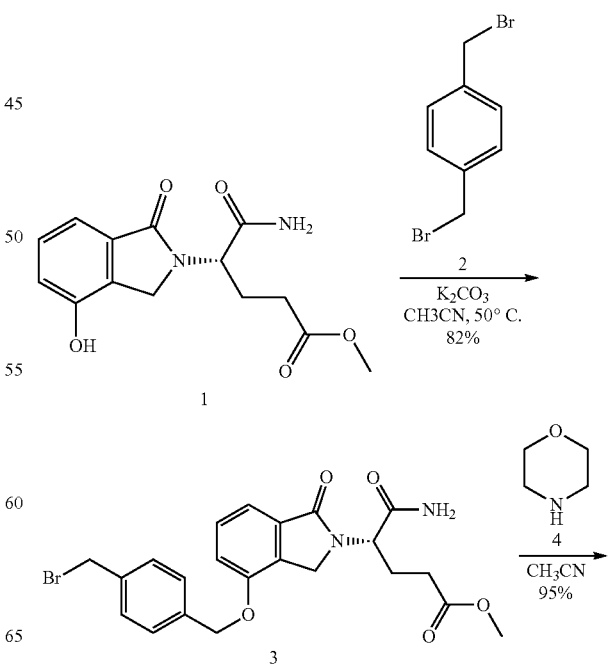

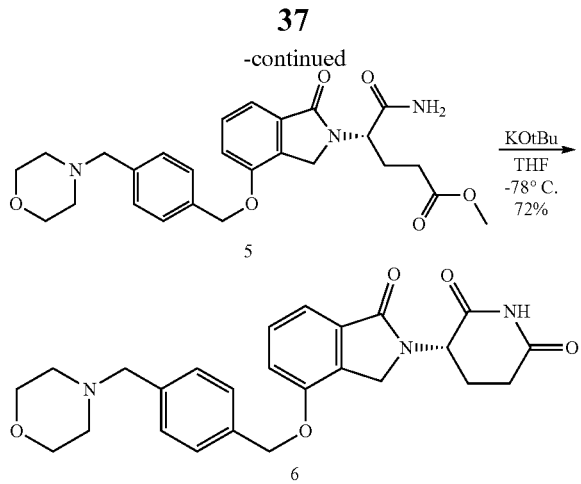

The synthesis started with optically pure (S) 3-(4-hydroxy-1-oxo-1,3-dihydroisoindol-2-yl)piperidine-2,6-dione (1), which was alkylated with 1,4-bis(bromomethyl)benzene (2) in the presence of potassium carbonate to furnish bromide 3. Reaction of the bromide (3) with morpholine (4) afforded 5 in good yield. Subsequent cyclization of 5 with potassium tert-butoxide at −78° C. proceeded to give imide 6 in a yield of 82% with the chiral center intact.

Experimental

4-[4-(4-bromomethylbenzyloxy)-1-oxo-1,3-dihydro-isoindol-2-yl]-4-carbamoylbutyric acid methyl ester (3): In a 2-L round bottom flask were charged (S)-methyl 5-amino-4-(4-hydroxy-1-oxoisoindolin-2-yl)-5-oxopentanoate (1) (30 g, 103 mmol), 1,4-bis(bromomethyl)benzene (2) (81 g, 308 mmol), potassium carbonate (14.19 g, 103 mmol) and acetonitrile (1.2 L). The mixture was stirred at 50° C. for 12 hours then cooled to room temperature. The mixture was filtered and the filtrate was concentrated on rota-yap. The resulting solid was dissolved in CH2Cl2 and purified on silica gel columns eluted with CH2Cl2/MeOH to give 4-[4-(4-bromomethylbenzyloxy)-1-oxo-1,3-dihydro-isoindol-2-yl]-4-carbamoylbutyric acid methyl ester (3) as white solid (40 g, 82% yield): 1H NMR (DMSO-d6) δ 1.98-2.13 (m, 1H, CHH), 2.14-2.23 (m, 1H, CHH), 2.23-2.32 (m, 2H, CHH, CHH), 3.50 (s, 3H, CH3), 4.34-4.63 (m, 2H, CH2), 4.67-4.80 (m, 3H, CH2, NCH), 5.25 (s, 4H, CH2), 7.19 (s, 1H, NHH), 7.24-7.34 (m, 2H, Ar), 7.41-7.54 (m, 5H, Ar), 7.58 (br. s, 1H, NHH).

4-carbamoyl-4-[4-(4-morpholin-4-ylmethyl-benzyloxy)-1-oxo-1,3-dihydro-isoindol-2-yl]-butyric acid methyl ester (5): To the CH2Cl2 solution of methyl 5-amino-4-(4-(4-(bromomethyl)benzyloxy)-1-oxoisoindolin-2-yl)-5-oxopentanoate (3) (36.5 g, 77 mmol) was added morpholine (4) (14.72 ml, 169 mmol) at room temperature. The mixture was stirred at room temperature for 1 hour. The resulting suspension was filtered and the filtrate was concentrated on rota-yap. The resulted oil was dissolved in EtOAc and washed with water (50 mL×3). The organic layer was concentrated on rota-yap to give 4-carbamoyl-4-[4-(4-morpholin-4-ylmethyl-benzyloxy)-1-oxo-1,3-dihydro-isoindol-2-yl]-butyric acid methyl ester (5) as a foamy solid (39 g, 95% yield): 1H NMR (DMSO-d6) δ 2.00-2.12 (m, 1H, CHH), 2.14-2.22 (m, 1H, CHH), 2.22-2.29 (m, 2H, CHH, CHH), 2.30-2.39 (m, 4H, CH2, CH2), 3.46 (s, 2H, CH2), 3.50 (s, 3H, CH3), 3.53-3.63 (m, 4H, CH2, CH2), 4.28-4.59 (m, 2H, CH2), 4.73 (dd, J=4.7, 10.2 Hz, 1H, NCH), 5.22 (s, 2H, CH2), 7.14-7.23 (m, 1H, NHH), 7.26-7.39 (m, 4H, Ar), 7.41-7.51 (m, 3H, Ar), 7.58 (s, 1H, NHH).

3-[4-(4-morpholin-4-ylmethyl-benzyloxy)-oxo-1,3-dihydro-isoindol-2-yl]-piperidine-2,6-dione (6): To the THF solution of methyl 5-amino-4-(4-(4-(morpholinomethyl)benzyloxy)-yl-oxoisoindolin-2-yl)-5-oxopentanoate (5) (40 g, 83 mmol), was added potassium tert-butoxide (9.80 g, 87 mmol) at −78° C. The mixture was stirred at this temperature for 30 minutes. To the reaction mixture, was added 45 mL of 1N HCl solution, followed by 200 mL of saturated NaHCO3 solution. The mixture was diluted with 500 mL of EtOAc at 0° C., stirred for 5 minutes and separated. The organic layer was washed with water (50 mL×3), brine (100 mL) and concentrated on rota-yap to give a white solid, which was stirred in diethyl ether (300 mL) to give a suspension. The suspension was filtered to give 3-[4-(4-morpholin-4-ylmethyl-benzyloxy)-oxo-1,3-dihydro-isoindol-2-yl]-piperidine-2,6-dione (6) as white solid (28.5 g, 72% yield): HPLC: Waters Symmetry C18, 5 μm, 3.9×150 mm, 1 mL/min, 240 nm, gradient to 95/5 acetonitrile/0.1% H3PO4 in 5 min: T=4.78 min (98.5%); mp: 209-211° C.; 1H NMR (DMSO-d6) δ 1.86-2.09 (m, 1H, CHH), 2.29-2.38 (m, 4H, CH2, CH2), 2.44 (dd, J=4.3, 13.0 Hz, 1H, CHH), 2.53-2.64 (m, 1H, CHH), 2.82-2.99 (m, 1H, CHH), 3.46 (s, 2H, CH2), 3.52-3.61 (m, 4H, CH2, CH2), 4.18-4.51 (m, 2H, CH2), 5.11 (dd, J=5.0, 13.3 Hz, 1H, NCH), 5.22 (s, 2H, CH2), 7.27-7.38 (m, 5H, Ar), 7.40-7.53 (m, 3H, Ar), 10.98 (s, 1H, NH); 13C NMR (DMSO-d6) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: M+1 465; Anal Calcd for C25H27N3O5+0.86 H2O: C, 64.63; H, 6.22; N, 9.04. Found: C, 64.39; H, 6.11; N, 8.89; H2O, 3.24.

6.2 Crystallization of CRBN-DDB1 with Compound B

The purification of CRBN-DDB1 for crystallization was performed as previously described in Matyskiela et al., Nature 2016, 535 (7611), 252-7. Crystallization of CRBN-DDB1 with Compound B was performed using sitting-drop vapor diffusion. 30 mg/mL CRBN-DDB1 in the presence of 1 mM Compound B was mixed 1:1 with, and subsequently equilibrated against, a mother liquor containing 200 mM sodium fluoride and 20% PEG 3350 at 20 C. Crystals were cryoprotected in the reservoir solution supplemented with 20% ethylene glycol and cooled under liquid nitrogen. Data was collected at the Advance Photon Source beamline LS-CAT 21ID-F. The complex crystal structure was solved by molecular replacement using Phaser with search model of 4TZ4 (see Chamberlian et al., Nature structural & molecular biology 2014, 21 (9), 803-9). Subsequent manual model building using Coot and refinement were performed using Refmac5 (see Emsley et al., Acta crystallographica. Section D, Biological crystallography 2011, 67 (Pt 4), 355-67).

6.3 TR-FRET Assay

The 6×His-tagged full length human CRBN bound to full length human DDB1 used in the assay was purified as described elsewhere with the exception that the thrombin cleavage/ortho nickel step is removed. In the assay, 60 nM 6×his-tagged CRBN-DDB1 was combined with 30 nM cy5-conjugated cereblon modulator and 3 nM LanthaScreen® Eu-anti-His Tag Antibody (ThermoFisher catalog #PV5596) in 20 mM HEPES pH 7, 150 mM NaCl, 0.005% Tween-20 assay buffer. FRET is observed by exciting at 340 nm and monitoring emission at 615 nm (non-FRET emission) and 665 nm (FRET emission), and FRET efficiency is determined by the ratio of FRET to non-FRET emission (665 nm/615 nm). Competing cereblon modulating compound or DMSO carrier is titrated and incubated for 10 minutes before scanning on the Envision plate reader with a 60 μsec delay to quantitate loss of FRET efficiency.

6.4 Cell-Based Chemiluminescent Substrate Degradation Assays

DF15 multiple myeloma cells expressing cereblon substrates Ikaros, Aiolos, and GSPT1 fused to an ePL tag (DiscoverX) were dispensed into a 384-well plate (Corning #3712) pre-spotted with compound. Compounds were dispensed by an acoustic despenser (ATS Acoustic Transfer System from EDC Biosystems) into a 384-well plate in a 10 point dose response curve using 3 fold dilutions starting at 10 μM and going down to 0.0005 μM. Twenty-five μL of media (RPMI-1640+10% Heat Inactivated FBS+25 mM Hepes+1 mM Na Pyruvate+1×NEAA+0.1% Pluronic F-68+ 1× Pen Strep Glutamine) containing 5000 cells was dispensed per well. Assay plates were incubated at 37° C. with 5% CO2 for four hours. After incubation, 25 μl of the InCELL Hunter™ Detection Reagent Working Solution (DiscoverX, cat #96-0002, Fremont, Calif.) was added to each well and incubated at room temperature for 30 minutes protected from light. After 30 minutes, luminescence was read on a PHERAstar luminometer (Cary, N.C.). To determine the EC50 value of a compound for the degradation of a given substrate (the half maximum effective concentration), a four parameter logistic model (Sigmoidal Dose-Response Model) (FIT=(A+((B−A)/1+((C/x)^D)))) where C is the inflection point (EC50), D is the correlation coefficient, and A and B are the low and high limits of the fit respectively) was used. All percent of control substrate degradation curves were processed and evaluated using Activity Base (IDBS).

6.5 Immunoblot Analysis of Endogenous Substrate Protein Levels $1 \times 10^6$ cells (either DF15 and OPM2) were treated with lenalidomide, pomalidomie, or Compound B for 5 hours before harvest. After quick 1× cold PBS rinse, cells were lysed by cell lysis buffer (Cell Signaling's Technologies). 10 ug of total lysate was loaded in each lane. Proteins were transferred to nitrocellulose membrane using Bio-Rad's Turbo System. Antibodies used in the Western included: Ikaros (14859S, Cell Signaling Technologies), Aiolos (15103S, Cell Signaling Technologies), actin (A5316, Sigma) and CRBN (in house antibody from Celgene).

6.6 Compound B Exhibits High Affinity to CRBN

Figure 3A:
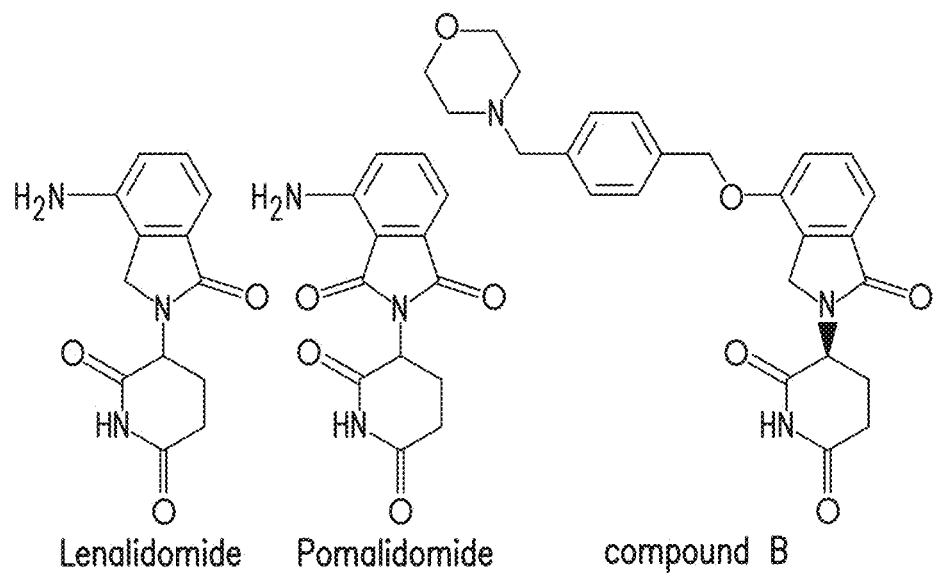
FIG. 3 depicts the relative cereblon binding affinities for Compound B, lenalidomide, and pomalidomide by TR-FRET. IC50s under these conditions were 1.5 μM for lenalidomide (circles), 1.2 μM for pomalidomide (diamonds), and 60 nM for Compound B (squares).
Figure 3B:
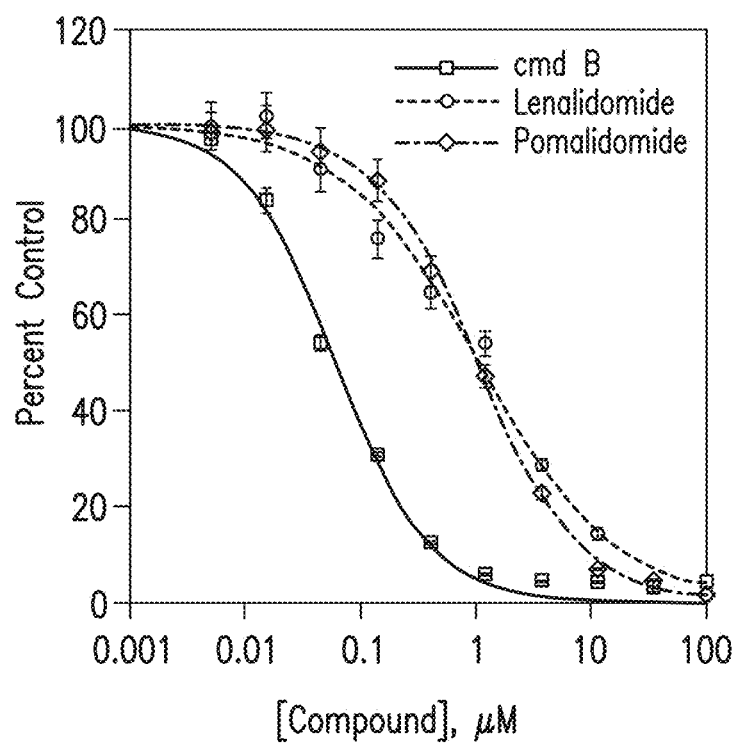

Like lenalidomide and pomalidomide, Compound B contains a glutarimide ring that binds in the tri-trp pocket of cereblon, and an isoindolinone ring that can interact with both cereblon and substrates. In addition, the chemical structure of Compound B is extended compared to lenalidomide and pomalidomide, containing additional phenyl and morpholino moieties enabling further interactions with cereblon or substrates (see FIG. 3). To determine the relative binding affinities between lenalidomide, pomalidomide, and Compound B, we used a TR-FRET cereblon binding assay (described above in Section 6.3) to determine the IC50 values for the these compounds. This assay monitors the displacement of a Cy5-conjugated cereblon modulating compound from the tri-trp pocket of CRBN. Under these assay conditions, the IC50 values for lenalidomide and pomalidomide were similar at 1.5 μM and 1.2 μM, respectively, while Compound B exhibited significantly higher affinity with an IC50 of approximately 60 nM (see FIG. 3).

6.7 Compound B has Greater Potency in Cellular Degradation Assay

Figures 4A, 4B:
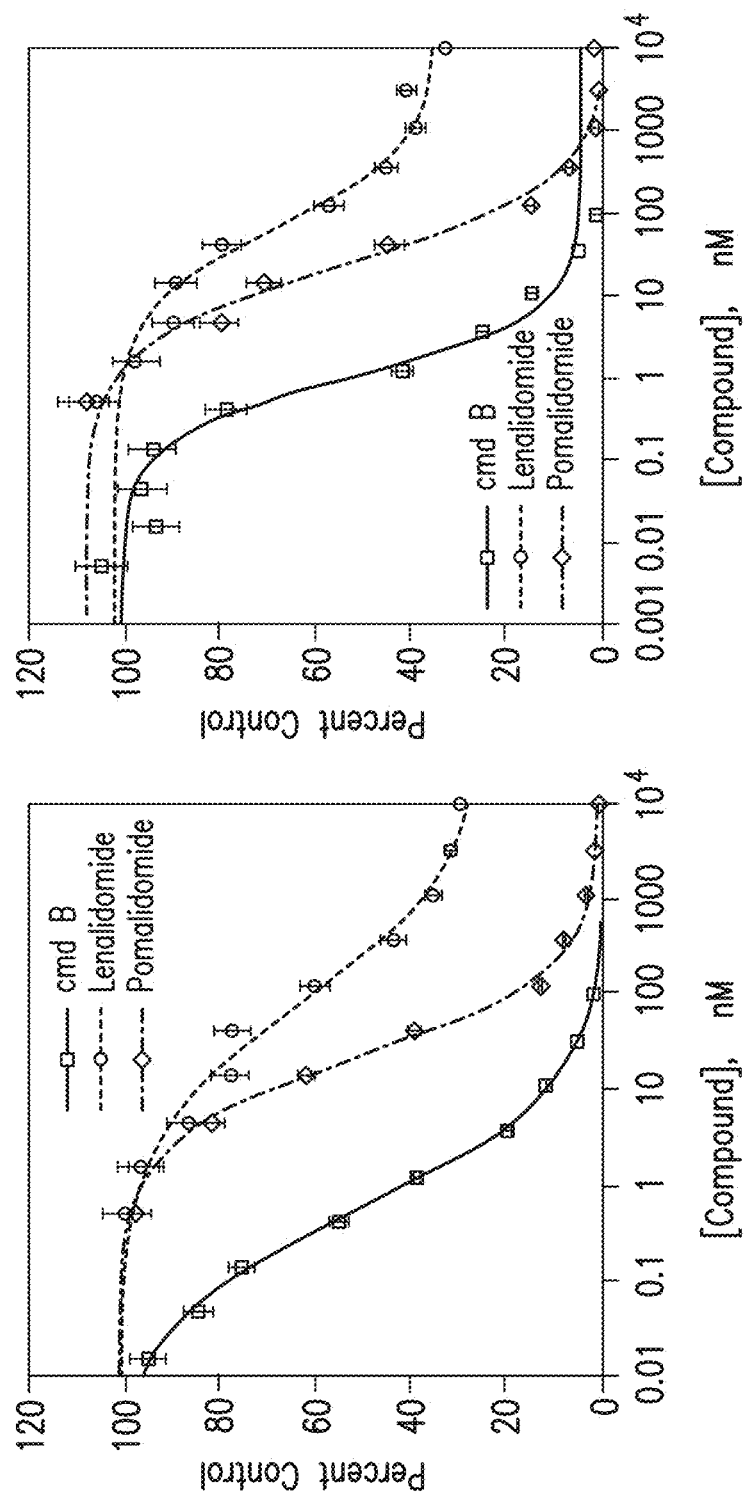
FIG. 4 depicts substrate degradation by Compound B. Part a) shows quantitation of Ikaros degradation with chemi-
Figure 4C:
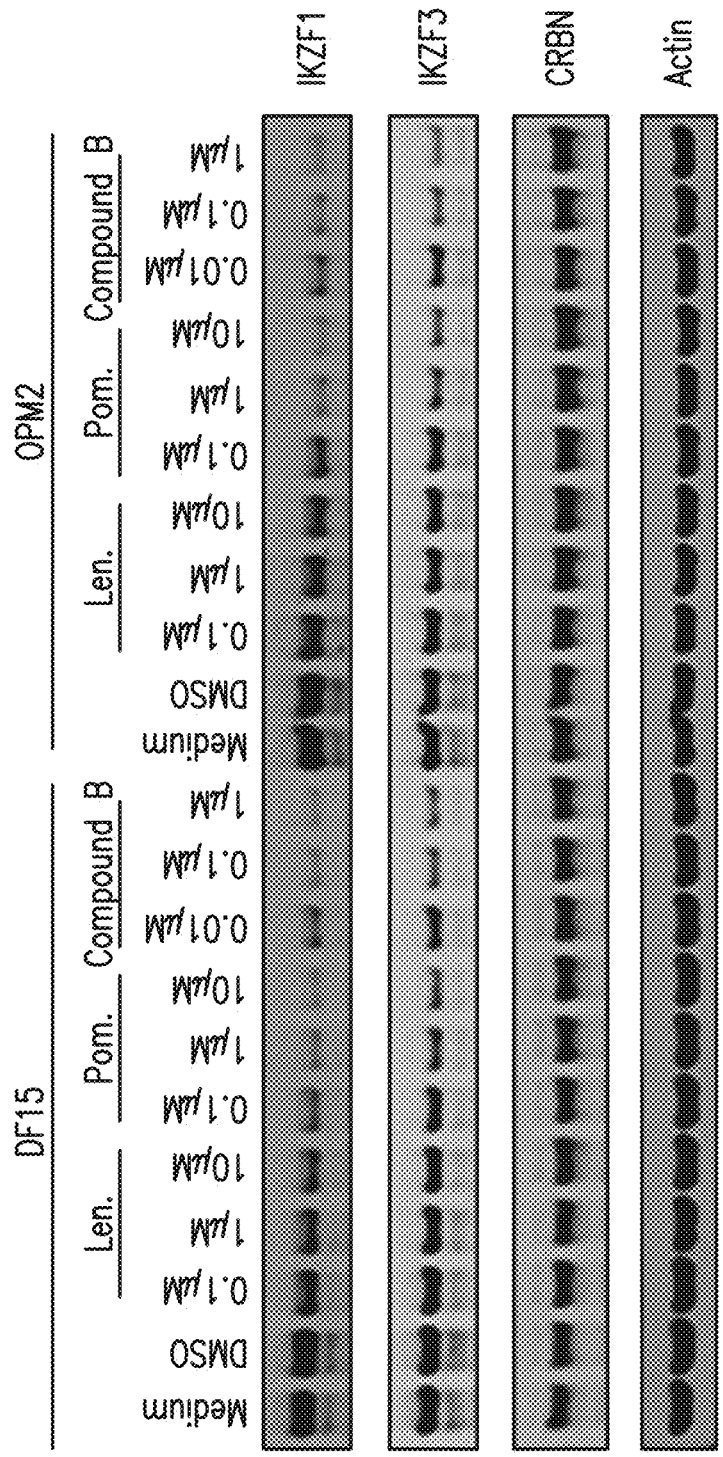

Consistent with increased biochemical binding affinity, Compound B also exhibited greater potency in cellular degradation assays measuring the ligand-dependent depletion of Ikaros or Aiolos (see FIG. 4 in parts a) and b)). However, Compound B does not significantly degrade GSPT1 or CK1α. To measure the effects of compound treatment on Ikaros and Aiolos degradation in cells, we used a cell-based assay that follows the chemiluminescent signal of proteins incorporating an ePL tag. We find that treatment with Compound B results in the loss of Ikaros protein levels with an EC50 of 1 nM, compared to 67 nM for lenalidomide and 24 nM for pomalidomide. Compound B is similarly potent towards Aiolos, with an EC50 of 0.5 nM compared to 87 nM for lenalidomide and 22 nM for pomalidomide. In addition, the extent of substrate depletion is more dramatic with Compound B, indicating more efficient substrate degradation relative to the rate of protein re-synthesis. The increase of the cellular degradation potency of Compound B corresponds with the increase in binding affinity observed in the biochemical assay, suggesting that the increase in cereblon affinity likely contributes to the increase in cellular potency. In contrast, the 3-4-fold increase in cellular potency observed for pomalidomide compared to lenalidomide is more likely driven by other factors such as the alteration of substrate affinity.

To confirm these effects are relevant with respect to the endogenous proteins, we treated DF15 and OPM2 cells with lenalidomide, pomalidomide, and Compound B for 5 hrs. Compound B treatment led to greater degradation of Ikaros and Aiolos compared to lenalidomide and pomalidomide (see FIG. 4 in part c)), consistent with the results from the chemiluminescence-based cellular degradation assay.

6.8 Crystal Structure of CRBN in Complex with DDB1 and Compound B

To examine the mechanism of higher affinity binding by Compound B, we determined the crystal structure of the ternary complex of Compound B bound to human cereblon (a.a. 40-442) and human DDB1 (full length) at 3.1A resolution (see part a) in FIG. 5). The overall structure was highly similar to the cereblon-DDB1 structures previously reported by us, with the binding site for cereblon modulators on the opposite face of cereblon compared to the DDB1 interaction site.

The glutarimide ring of Compound B binds in the tri-trp pocket in a similar binding mode to lenalidomide, pomalidomide and 1-(3-chloro-4-methylphenyl)-3-((2-(2,6-dioxopiperidin-3-yl)-1-oxoisoindolin-5-yl)methyl)urea (Compound C), and the isoindolinone ring is presented on the surface in a similar binding mode to lenalidomide (FIG. 5), pomalidomide, and Compound C. Compound B has an extended structure compared to lenalidomide and pomalidomide, and the crystal structure shows that the phenyl ring of Compound B is positioned inside a groove on the cereblon surface formed by E377, H378, P352 and H353. The morpholine ring is oriented towards a hydrophobic pocket formed of residues I154 and F102, however this moiety is poorly defined in the electron density, possibly due to motion. F150 is positioned adjacent to the morpholino group of Compound B, in contrast to some other structures where this is found in an extended conformation. However, this conformation should be interpreted with caution as F150 occurs at the apex of a loop that has exhibited mobility in other structures, and often participates in crystal lattice contacts.

The structures of cereblon in complex with CK1α and GSPT1 revealed that the primary site of cereblon substrate interactions is shared between the characterized substrates, and docking and mutagenesis studies predicted the same site of interaction for Ikaros and Aiolos. This site of interaction is formed by three hydrogen bond donors on cereblon, N351, H357, and W400, which are positioned proximal to the isoindolinone or phthalimide rings of bound cereblon modulators. These residues are positioned away from the phenyl and morpholine rings of Compound B, such that differences in compound activity are unlikely to be the result of direct substrate interactions of these moieties with Ikaros or Aiolos. Instead, a comparison of the crystal structures of lenalidomide and Compound B bound to cereblon-DDB1 reveals that the observed increase in affinity correlates well with the increased surface interactions between Compound B and cereblon (see part b) of FIG. 5).

Throughout this application various publications have been referenced. The disclosures of these publications in their entireties are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A method of measuring the affinity of a compound to cereblon (CRBN) or determining if a compound binds to cereblon (CRBN), the method comprising:
    contacting the compound with a complex, wherein the complex comprises
        (i) a CRBN having a europium-anti-his antibody on the N-terminus of the CRBN, and
        (ii) a Cy5-conjugated small molecule, wherein the Cy5-conjugated small molecule binds the CRBN;
    measuring fluorescence resonance energy transfer (FRET) after contacting the compound with the complex; and
    determining the binding and/or affinity of the compound to CRBN based on the measured FRET; and
    wherein the Cy5-conjugated small molecule has a structure of Formula (I)

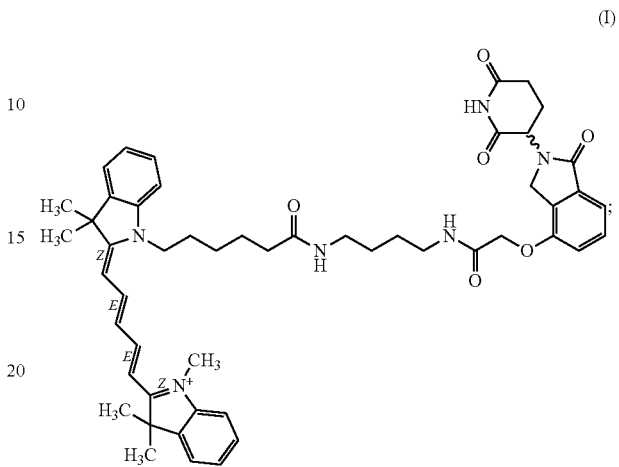

wherein the Cy5-conjugated small molecule binds in a hydrophobic tri-tryptophan pocket formed by Trp380, Trp386, and Trp400 on the CRBN.

2. The method of claim 1, wherein the complex further comprises a DNA damage-binding protein 1 (DDB1).

3. The method of claim 1, wherein the method further comprises measuring FRET prior to contacting the compound with the complex.

4. The method of claim 3, further comprises determining that the compound binds to the CRBN if FRET is reduced after contacting the compound with the complex.

5. The method of claim 1, wherein FRET is observed by exciting at 340 nm and monitoring emission at 615 nm (non-FRET emission) and 665 nm (FRET emission).

6. The method of claim 5, wherein a first FRET efficiency is determined prior to contacting the compound with the complex, and a second FRET efficiency is determined after contacting the compound with the complex, and wherein FRET efficiency is the ratio of FRET emission at 665 nm to non-FRET emission at 615 nm.

7. The method of claim 6, further comprises determining that the compound binds to the CRBN if the second FRET efficiency is less than the first FRET efficiency.

* * * * *